United States Patent
Vincent-Aubry

(10) Patent No.: US 7,954,636 B2
(45) Date of Patent: Jun. 7, 2011

(54) INTRAOCULAR LENS INJECTOR ASSEMBLY

(75) Inventor: Francoise Vincent-Aubry, Mevoisins (FR)

(73) Assignee: Laboratoire de Contactologie Appliquee, Chartres (FR)

( * ) Notice: Subject to any disclaimer, the term of this patent is extended or adjusted under 35 U.S.C. 154(b) by 971 days.

(21) Appl. No.: 11/579,244

(22) PCT Filed: May 4, 2005

(86) PCT No.: PCT/FR2005/050303
§ 371 (c)(1), (2), (4) Date: Oct. 30, 2006

(87) PCT Pub. No.: WO2005/110289
PCT Pub. Date: Nov. 24, 2005

(65) Prior Publication Data
US 2007/0250068 A1    Oct. 25, 2007

(30) Foreign Application Priority Data
May 6, 2004 (FR) .................... 04 50874

(51) Int. Cl.
*B65D 83/10* (2006.01)
(52) U.S. Cl. ........ 206/364; 206/438; 206/571; 623/6.12
(58) Field of Classification Search .......... 206/438, 206/306, 571, 210, 5.1, 363–365; 623/6.11–6.64; 606/107
See application file for complete search history.

(56) References Cited

U.S. PATENT DOCUMENTS

| | | | | |
|---|---|---|---|---|
| 1,378,806 A * | 5/1921 | Ausubel | ......................... | 206/210 |
| 1,919,811 A * | 7/1933 | Stonebraker | ................... | 206/306 |
| 2,812,231 A * | 11/1957 | Zar | ................................. | 422/26 |
| 3,112,747 A * | 12/1963 | Cowley | ......................... | 604/197 |
| 4,787,904 A | 11/1988 | Severin et al. | | |
| 5,313,858 A * | 5/1994 | Stitt | ................. | 81/3.55 |
| 5,407,070 A * | 4/1995 | Bascos et al. | ................. | 206/365 |
| 5,934,460 A * | 8/1999 | Schmid | ......................... | 206/210 |
| 6,228,324 B1 * | 5/2001 | Hasegawa et al. | .............. | 422/30 |
| 6,866,142 B2 * | 3/2005 | Lamborne et al. | ............. | 206/0.6 |
| 2004/0117012 A1 * | 6/2004 | Vincent | ......................... | 623/6.12 |
| 2007/0000801 A1 * | 1/2007 | Mauran et al. | ................. | 206/438 |

FOREIGN PATENT DOCUMENTS

| | | |
|---|---|---|
| FR | 2 789 890 A1 | 5/2000 |
| WO | WO 03/044946 A2 | 5/2003 |
| WO | WO 03/049645 A2 | 6/2003 |

* cited by examiner

*Primary Examiner* — Mickey Yu
*Assistant Examiner* — Chun Cheung
(74) *Attorney, Agent, or Firm* — Sughrue Mion, PLLC

(57) ABSTRACT

An assembly comprising a packaging device (20) and an intraocular lens injector (10) comprising a body (11) that contains an intraocular lens, said packaging device (20) being for receiving and storing said injector (10) prior to use, said packaging device (20) being made of a material that is waterproof, and being filled with a storage solution for maintaining at least the body (11) of said injector (10) and the intraocular lens in total immersion throughout the duration of storage, said packaging device (20) comprising a substantially rigid container (21, 22) and an opening (25) for enabling said injector (10) to be installed and removed, said container (21, 22) including at least one internal shoulder (26, 27) co-operating with a portion of the injector (10) to center and maintain its lens ejector end (14) away from the walls of said container (21, 22).

20 Claims, 4 Drawing Sheets

INTRAOCULAR LENS INJECTOR ASSEMBLY

The present invention relates to a packaging device for an intraocular lens injector, and more particularly the invention relates to an assembly comprising such a packaging device and such an injector.

It is well known to use an injector for injecting an intraocular lens, e.g. during an ophthalmological cataract operation. In order to improve such systems, proposals have been made to provide prepackaged single-use injectors so that the user need only open the package containing the injector and then make use of the injector directly for injecting the lens. The lens may be placed in a cassette for inserting in the injector or it may be placed directly in the body of said injector. Dispenser means, generally comprising a piston that can be moved by hand, are provided so as to enable the user to dispense said lens through said injector directly into the eye of a patient during an ophthalmological surgical operation. That kind of device must naturally be stored in sterile manner before it is used. Proposals have been made to fill the inside of the injector with liquid and to provide the endpiece of said injector with a plug. It has been found that that type of device tends to empty in the long term, in particular because of lack of sealing via gaskets, and also because of the way polypropylene, the material generally used for making injectors, is far from constituting a perfect barrier to water vapor. Proposals have also been made to place injectors in flexible pouches filled in a storage liquid or solution. By way of example, such an assembly is described in U.S. Pat. No. 4,787,904. Nevertheless, that configuration presents drawbacks, relating in particular to difficulties of guaranteeing good mechanical protection for the injector which is itself fragile, and also concerning performing sterilization appropriately. Sterilization is generally performed using wet heat in a steam pressure autoclave, and the temperature and pressure differences that occur at the end of sterilization can be harmful for the integrity of such flexible pouches, which makes it necessary to use more complex sterilization equipment operating with pressure and counterpressure or with a spray of superheated water. Furthermore, making double sterile packaging of the kind required for surgery can hardly be envisaged with flexible pouches. Similarly, the use of flexible pouches can present a risk of evaporation through the wall of the receptacle, which is prejudicial to maintaining the properties of the injector over the long term. Loss of liquid, e.g. by evaporation of the storage liquid through said flexible pouch, can lead to degradation in the properties of the injector itself, e.g. in the event of it coming into contact with air. It is also possible to mention problems of plastics material aging and the risk of loosing the liquid contained inside the injector itself. Packaging implemented in the form of flexible pouches is also sensitive to accidental breakage, e.g. during transport or during other manipulations, and it is not always obvious for the final user to verify absolute integrity of the container of the injector at the time it is used. For example, microleaks are not always visible when flexible pouches are used. Similarly, storing the injector in a flexible pouch filled with liquid is not very practical at the time the pouch is opened by the final user, there being considerable risk of said liquid leaking away when the package is opened.

An object of the present invention is to provide an assembly comprising an intraocular lens injector and a packaging device that does not reproduce the above-mentioned drawbacks.

More particularly, an object of the present invention is to provide such an assembly that is entirely proof against water and proof against water vapor, even over storage of long duration.

The present invention is to provide such an assembly that can withstand impacts and avoid any damage to the injector contained in the packaging device, during transport or any other handling that might be performed prior to final use of the injector.

Another object of the invention is to provide such an assembly that is simple and inexpensive to manufacture and assemble, and that is easy for the final user to use.

The present invention also seeks to provide such an assembly that is easy and reliable to sterilize properly.

The present invention thus provides an assembly comprising a packaging device and an intraocular lens injector comprising a body that contains an intraocular lens, said packaging device being for receiving and storing said injector prior to use, said packaging device being made of a material that is waterproof, and being filled with a storage solution for maintaining at least the body of said injector and the intraocular lens in total immersion throughout the duration of storage, said packaging device comprising a substantially rigid container and an opening for enabling said injector to be installed and removed, said container including at least one internal shoulder co-operating with a portion of the injector to center and maintain its lens ejector end away from the walls of said container.

Advantageously, said packaging device comprises a flask closed by a plug, in particular an elastomer plug.

Advantageously, said plug is secured on said flask by means of a capsule, in particular a crimp-on metal capsule.

In another embodiment of the present invention, said packaging device comprises a blister-pack container closed by a leakproof membrane, in particular an aluminum membrane.

Advantageously, said storage solution is water, a physiological saline solution, or a viscoelastic solution.

Advantageously, said material is glass.

In a variant, said material is a synthetic material presenting a high degree of leakproofing against water vapor.

Advantageously, the packaging device is filled with the storage solution in such a manner that the body of the injector is fully immersed in all positions of said packaging device.

Advantageously, said injector comprises a body having an approximately cylindrical portion receiving the lens in substantially non-deformed manner, an approximately frusto-conical intermediate portion for folding the lens, and a lens-ejector end portion, the injector also comprising dispenser means manually movable within said body to move the lens from the approximately cylindrical portion of the body towards the ejector end portion of the body, and subsequently to eject it, said body having at its end remote from the ejector end a radially-projecting flange suitable for co-operating with an internal shoulder provided in the packaging device for positioning said injector in said packaging device in such a manner that its ejector end is held apart from the walls of the packaging device and the body is completely immersed in said storage solution, in any position of said packaging device.

Advantageously, said packaging device is substantially transparent.

Advantageously, said assembly is adapted to be subjected to sterilization by wet heat, in particular in a steam pressure autoclave.

Other characteristics and advantages of the invention appear more clearly from the following detailed description made with reference to the accompanying drawings given as non-limiting examples, and in which.

According to the invention, the assembly comprises an injector 10 containing an intraocular lens, and a packaging device 20 comprising a container 21, 22.

Figure 1:
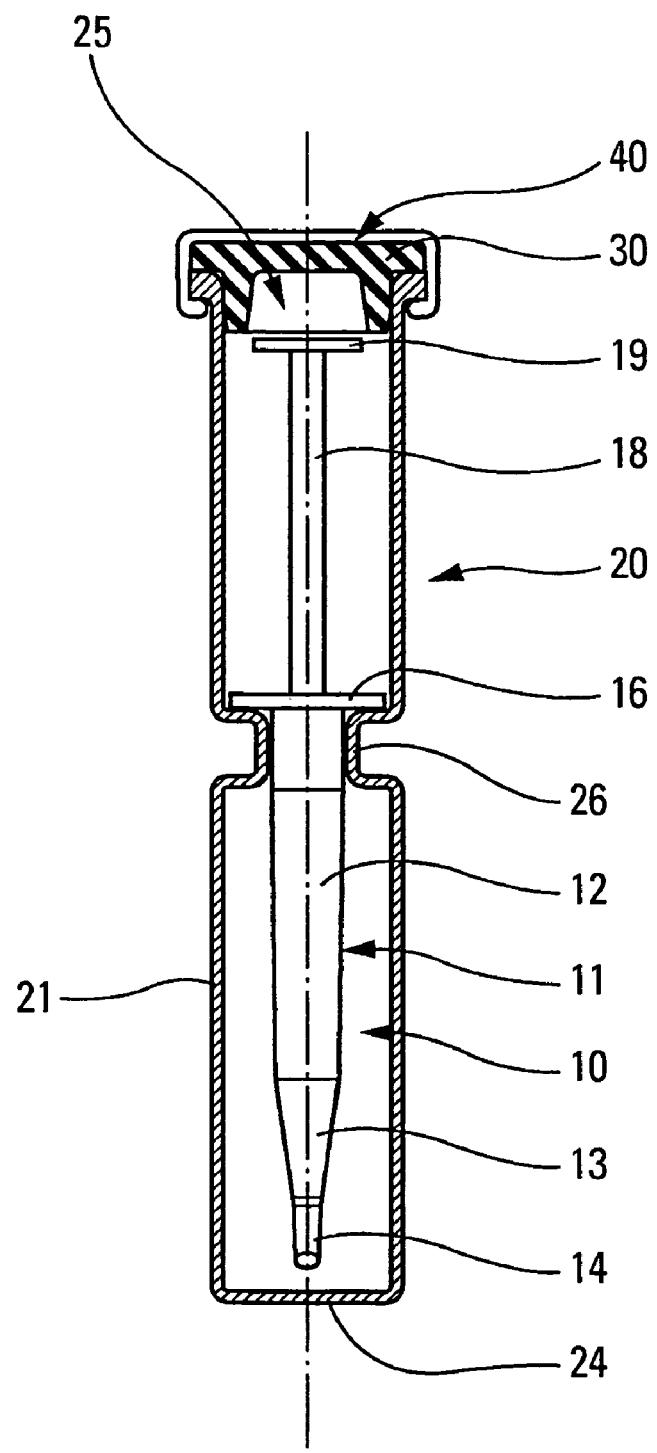
FIG. 1 is a diagrammatic longitudinal section view of a packaging device for an intraocular injector in a first embodiment of the present invention.
Figure 2:
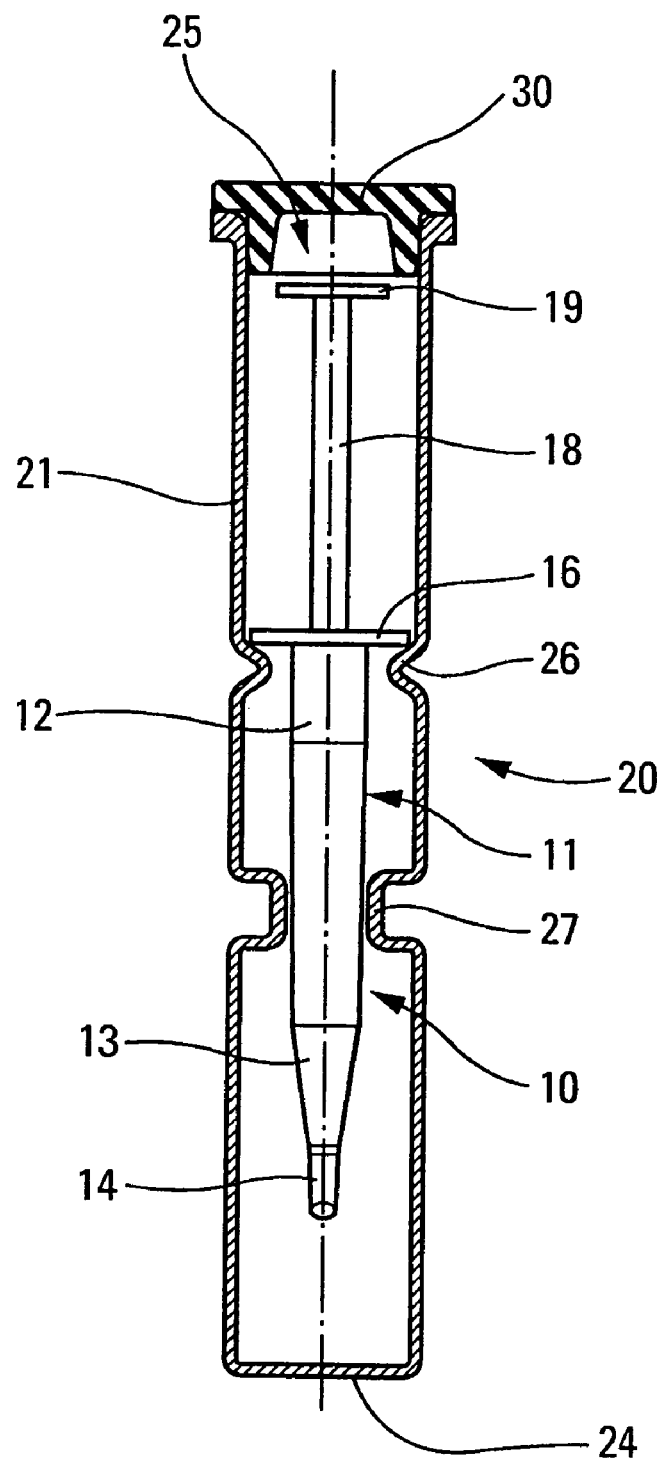
FIG. 2 is a diagrammatic view similar to FIG. 1, showing a variant of the first embodiment of FIG. 1.

FIGS. 1 and 2 show two variants of a first embodiment. In this first embodiment, the packaging device 20 has a preferably rigid container 21 advantageously made in the form of a flask having a plug 30. The plug 30 is placed in an opening 25 of said flask 21, and it may advantageously be secured to said flask by a crimp-on capsule 40, as shown in FIG. 1. The plug 30 may be an elastomer plug, of the kind approved for perfusions or the like.

Advantageously, the flask 21 is made of glass, which is a material that is completely leakproof against water vapor, and from which there is no loss of liquid, even after storage for a very long time, typically several years. In a variant, it is also be possible to use leakproof synthetic materials, for example high-performance plastics materials that provide a flask having both good stiffness and perfect ability to withstand evaporation of the liquid. The container or flask 21 is filled with a storage solution that may be water, a physiological saline solution, or a viscoelastic solution of the kind used in ophthalmic surgery. Advantageously, the container 21 has at least one internal shoulder co-operating with a portion of the injector 10 for the purposes both of centering it and of holding its lens-ejector end away from any of the walls of the container 21. More precisely, the injector as shown in the drawings advantageously comprises a body 11 having a cylindrical portion 12, a lens-ejector portion 14 forming the endpiece through which the lens is ejected, and a frustoconical portion 13 connecting said cylindrical portion 12 to said ejector portion 14. A radially-projecting flange 16 is advantageously provided at the end of said cylindrical portion 12 of the body 11 that is remote from the ejector endpiece 14. Dispenser means, comprising in particular a piston 18 provided with a plane driver surface 19 are advantageously provided to eject the lens (not shown) placed in the body of the injector. In general, the structure of the injector as described above is similar to that of a syringe.

In this embodiment, an internal shoulder 26 is advantageously provided in the flask or container 21 for co-operating with said radially-projecting flange 16 of the injector. As can be seen in FIGS. 1 and 2, this configuration guarantees absence of any contact between the ejector endpiece 14, i.e. the sensitive portion of the injector, and the walls of the container 21, and in particular is bottom wall 24. Such positioning of the injector thus guarantees effective protection of the ejector endpiece which is unable to bump against the walls of the flask, and in particular cannot strike the bottom wall of the flask. This internal shoulder thus serves to create a safe confined space for the injector 10 and serves to prevent any possibility of the ejector endpiece being spoilt, in particular while the assembly comprising the injector and the packaging device is being transported. Advantageously, a second internal shoulder 27 can be provided to further enhance positioning of the injector inside said flask 21, as can be seen in particular in FIG. 2. Naturally, FIGS. 1 and 2 merely show particular possible configurations, and others are therefore possible.

Advantageously, the storage solution is filled into the flask 21 up to a level such that even when the flask 21 is in a position other than the upright position shown in FIGS. 1 and 2, the entire body 11 together with the lens are fully immersed inside the container. In the embodiment of FIGS. 1 and 2, this means that the liquid needs to fill the container 21 in such a manner that even when the container 21 is in an upside-down position, with the ejector endpiece 14 situated at the top, the level of the liquid will always be situated above said ejector endpiece 14. Advantageously, the container or flask 21 is transparent, thus enabling the injector to be clearly visible from the outside.

Figure 3:
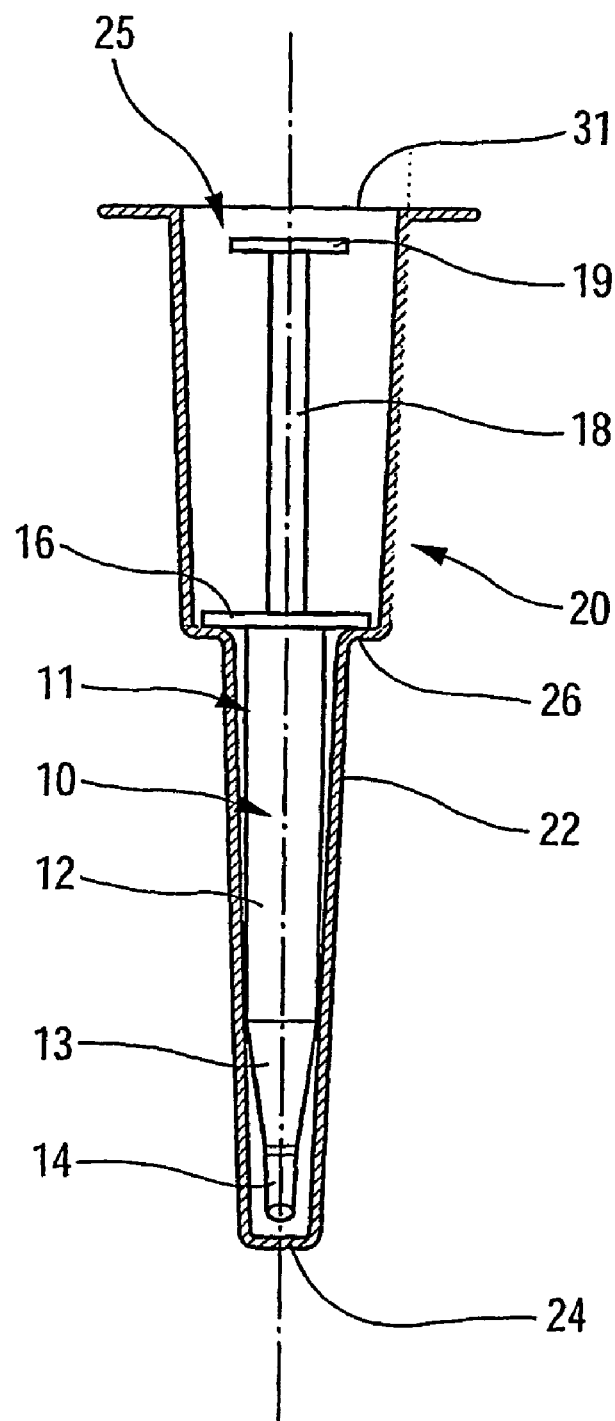
FIG. 3 is a diagrammatic view similar to FIGS. 1 and 2 showing a second embodiment of the present invention.
Figure 4:
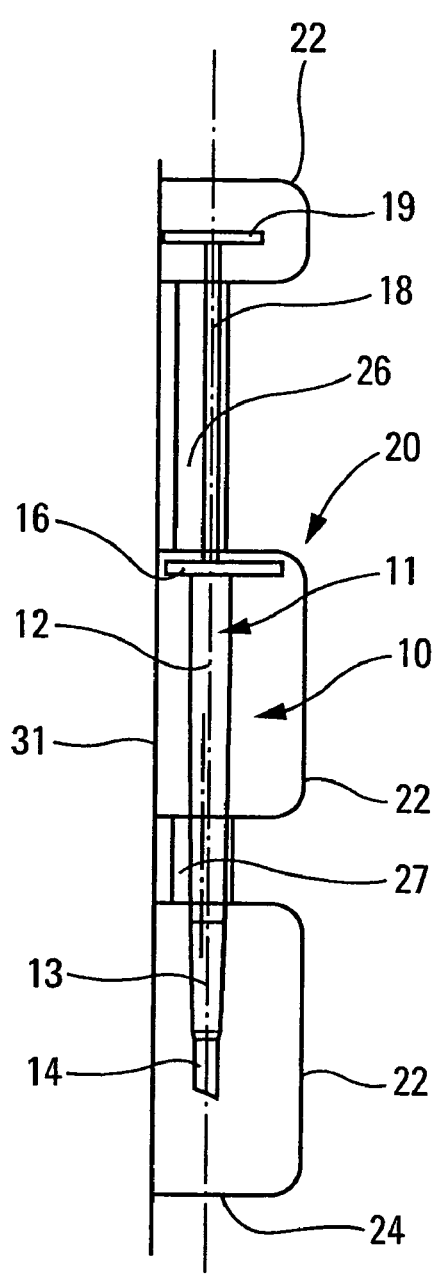
FIG. 4 is a diagrammatic longitudinal section view of a variant of the second embodiment shown in FIG. 3.
Figure 5:
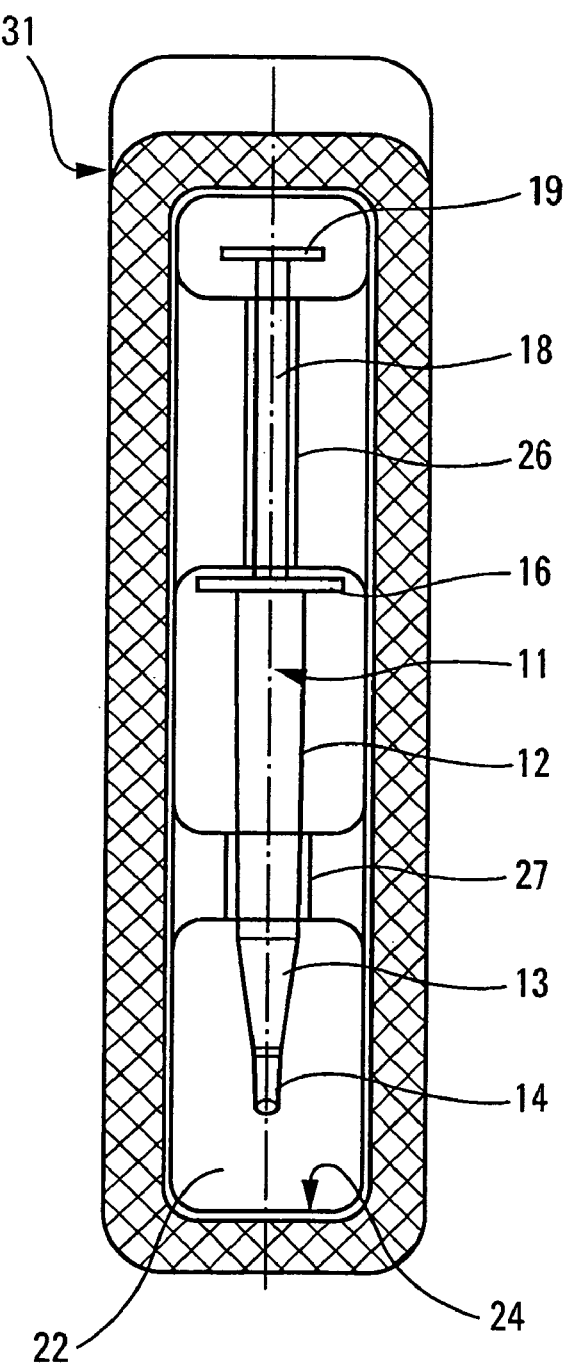
FIG. 5 is a view similar to that of FIG. 4, seen from a different point of view.

FIGS. 3 to 5 show a second embodiment. In this second embodiment, the packaging device 20 has a container 22 made in the form of a blister-pack that is closed by a leakproof membrane 31, in particular made of aluminum. The example of FIG. 3 shows a blister-type container of outside shape quite similar to that of the first embodiment shown in FIGS. 1 and 2, while FIGS. 4 and 5 show an embodiment that is quite different, in which the surface area covered by the membrane 31 is much larger. The outside shape of the container 22 proper could again be quite different from that shown. Advantageously, and as for the first embodiment, this blister or container 22 is preferably substantially rigid, and advantageously relatively transparent. It also advantageously has at least one shoulder 26 adapted to avoid any contact between the ejector endpiece 14 of the injector, and the walls of the container 22.

In the example of FIGS. 4 and 5, this shoulder 26 is formed by a narrowed portion 26 of the blister-pack that interconnects to larger portions 22 disposed firstly level with the radially-projecting flange 16 of the body 11 of the injector 10, and secondly level with the bearing surface 19 of the driver piston 18 of the injector. The example of FIGS. 4 and 5 also shows a third portion of enlarged size 22, situated in the vicinity of the ejector endpiece 14 for the purpose of guaranteeing complete absence of contact between the wall of the container and said ejector endpiece. An appropriate narrowing 26 may advantageously be provided between the second and third enlarged portions 22, as shown in FIGS. 4 and 5.

In a preferred embodiment, in which the container is substantially rigid, the present invention guarantees better sterility as provided by a rigid leaktight system. Because of the pressure and temperature differences that occur at the end of autoclaving, sterilization is withstood better in the context of a rigid container. It is then possible to perform a drying evacuation step in order to guarantee that the outer protective shell is intact, particularly when double sterile packaging is involved. The absence of any liquid escaping by evaporation through the wall of the receptacle or container is also advantageous. In comparison, the thin wall of a deformable receptacle, such as a flexible pouch, is much more permeable which can be more prejudicial to maintaining the properties of the injector over the long term. Similarly, the greater strength of the container of the invention against impacts and accidental breakage, in particular during transport or handling, is advantageous. The same applies to the lack of ambiguity concerning the integrity of the container containing the injector at the time it is used. There can be no possible suspicion of microleaks, as can occur with a blister-pack that has been slightly creased.

The present invention is particularly suitable for use with an injector in which the lens is already predisposed inside the body 11. Advantageously, the lens is placed in the body 11 in non-deformed manner, and it deforms inside the frustoconical portion 13 because of the pressure exerted by the user on the piston 18. This configuration makes the injector very simple to use for the final user, since all that needs to be done is to open the packaging device 20, to take hold of the drive surface 19 of the piston 18 in order to extract the injector from the packaging device 20, and then to actuate said injector so as to eject the lens it contains. There is no need to place the lens in the injector before it is used, whether directly or by using some accessory device.

Other modifications are also possible for the person skilled in the art without going beyond the ambit of the present invention as defined by the accompanying claims.

The invention claimed is:

1. An assembly comprising a packaging device (20) and an intraocular lens injector (10) comprising a body (11) that contains an intraocular lens, the assembly being characterized in that said packaging device (20) is for receiving and storing said injector (10) prior to use, said packaging device (20) being made of a material that is waterproof, and being filled with a storage solution for maintaining at least the body (11) of said injector (10) and the intraocular lens in total immersion throughout the duration of storage, said packaging device (20) comprising a substantially rigid container (21, 22) and an opening (25) for enabling said injector (10) to be installed and removed, said container (21, 22) including at least one internal shoulder (26, 27) co-operating with a portion of the injector (10) to center and maintain a lens ejector end (14) of the injector away from the walls of said container (21, 22);
wherein the packaging device is filled with the storage solution in such a manner that the body (11) of the injector (10) is fully immersed in all positions of said packaging device; and
wherein the least one internal shoulder is defined by a reduced diameter portion of the container, the diameter of the container being larger axially above and below the reduced diameter portion.

2. An assembly according to claim 1, in which said packaging device (20) comprises a flask (21) closed by a plug (30).

3. An assembly according to claim 2, in which said plug (30) is secured on said flask (21) by means of a capsule (40).

4. An assembly according to claim 1, in which said packaging device (20) comprises a blister-pack container (22) closed by a leakproof membrane (31).

5. An assembly according to claim 1, in which said storage solution is water, a physiological saline solution, or a viscoelastic solution.

6. An assembly according to claim 1, in which said material is glass.

7. An assembly according to claim 1, in which said material is a synthetic material presenting a high degree of leakproofing against water vapor.

8. An assembly according to claim 1, in which said injector (10) comprises a body (11) having an approximately cylindrical portion (12) receiving the lens in substantially non-deformed manner, an approximately frustoconical intermediate portion (13) for folding the lens, and a lens-ejector end portion (14), the injector (10) also comprising dispenser means (18) manually movable within said body (11) to move the lens from the approximately cylindrical portion (12) of the body (11) towards the ejector end portion (14) of the body (11), and subsequently eject the lens, said body (11) having at an end remote from the ejector end (14) a radially-projecting flange (16) suitable for co-operating with an internal shoulder (26) provided in the packaging device (20) for positioning said injector (10) in said packaging device in such a manner that the ejector end is held apart from the walls of the packaging device (20) and the body (11) is completely immersed in said storage solution, in any position of said packaging device (20).

9. An assembly according to claim 1, in which said packaging device (20) is substantially transparent.

10. An assembly according to claim 1, adapted to be subjected to sterilization by wet heat, in particular in a steam pressure autoclave.

11. The assembly according to claim 2, wherein the plug is an elastomer plug.

12. The assembly according to claim 3, wherein the plug is secured on said flask by a crimp-on metal capsule.

13. An intraocular lens injector assembly, comprising:
an intraocular lens injector comprising a body and a lens ejector end;
an intraocular lens contained in the body;
a packaging device in which the injector is stored prior to use, the packaging device is waterproof and filled with a storage solution for maintaining at least the body of the injector and the intraocular lens immersed in the solution during storage, the packaging device comprising a substantially rigid container and an opening through which the injector is installed for storage and removed for use, the container comprising at least one internal shoulder co-operating with a portion of the injector body to center and maintain the lens ejector end away from walls of the container;
wherein the packaging device is filled with the storage solution in such a manner that the body (11) of the injector (10) is fully immersed in all positions of said packaging device; and
wherein the least one internal shoulder is defined by a reduced diameter portion of the container, the diameter of the container being larger axially above and below the reduced diameter portion.

14. The assembly according to claim 13, wherein the packaging device comprises a flask closed by a plug.

15. The assembly according to claim 14, wherein the plug is secured on said flask by a crimp-on metal capsule.

16. The assembly according to claim 13, wherein the storage solution is water, a physiological saline solution, or a viscoelastic solution.

17. The assembly according to claim 13, wherein the material is glass.

18. The assembly according to claim 13, wherein the material is a synthetic material presenting a high degree of leakproofing against water vapor.

19. The assembly according to claim 13, wherein said injector body has a cylindrical portion receiving the lens in substantially non-deformed manner and a frustoconical intermediate portion for folding the lens, the injector also comprising a manually movable piston within the body to move the lens from the approximately cylindrical portion towards the ejector end, and to subsequently eject the lens.

20. An assembly including a packaging device storing an intraocular lens injector therein, wherein the intraocular lens injector includes a body and an intraocular lens disposed therein, said packaging device comprising:
a substantially rigid container made of a waterproof material so as to provide a completely leakproof container, having walls and an opening receiving the intraocular injector therein; and
an internal shoulder formed on the container, cooperating with a portion of the intraocular lens injector, to center and maintain a lens ejector end of the intraocular lens injector away from the walls of said container, wherein said internal shoulder is defined by a reduced inner diameter portion of the container, the container having a larger inner diameter portion that is larger axially above and below said reduced inner diameter portion, and wherein said container is filled with a storage solution in such a manner that the entire body of the intraocular lens injector is fully immersed in all positions of said packaging device, including when said container is in an upside-down position defined by when the lens ejector end is situated at the top of the assembly.

* * * * *